(12) United States Patent
Orbay et al.

(10) Patent No.: US 8,062,296 B2
(45) Date of Patent: *Nov. 22, 2011

(54) MODULAR FRACTURE FIXATION PLATE SYSTEM WITH MULTIPLE METAPHYSEAL AND DIAPHYSEAL PLATES

(75) Inventors: Jorge L. Orbay, Miami, FL (US); Javier E. Castaneda, Miami, FL (US); Edward Mebarak, Miami Beach, FL (US)

(73) Assignee: Depuy Products, Inc., Warsaw, IN (US)

( * ) Notice: Subject to any disclaimer, the term of this patent is extended or adjusted under 35 U.S.C. 154(b) by 1657 days.

This patent is subject to a terminal disclaimer.

(21) Appl. No.: 11/082,401

(22) Filed: Mar. 17, 2005

(65) Prior Publication Data
US 2006/0229619 A1  Oct. 12, 2006

(51) Int. Cl.
*A61B 17/56* (2006.01)
(52) U.S. Cl. .......................................... 606/71
(58) Field of Classification Search .................... 606/60, 606/280, 70, 71, 281, 286, 289, 291, 295, 606/301; 403/362
See application file for complete search history.

(56) References Cited

U.S. PATENT DOCUMENTS

| | | | |
|---|---|---|---|
| 1,105,105 A | 7/1914 | Sherman | |
| 2,406,832 A | 9/1946 | Hardinge | |
| 2,486,303 A | 10/1949 | Longfellow | |
| 3,488,779 A | 1/1970 | Christensen | |
| 3,695,259 A | 10/1972 | Yost | |
| 4,219,015 A | 8/1980 | Steinemann | |
| 4,506,662 A | 3/1985 | Anapliotis | |
| 4,683,878 A | 8/1987 | Carter | |
| 4,776,330 A | 10/1988 | Chapman et al. | |
| 4,781,183 A | 11/1988 | Casey et al. | |
| 4,867,144 A | 9/1989 | Karas et al. | |
| 4,955,886 A | 9/1990 | Pawluk | |
| 4,957,497 A | 9/1990 | Hoogland et al. | |
| 5,002,544 A | 3/1991 | Klaue et al. | |
| 5,015,248 A | 5/1991 | Burstein et al. | |
| 5,041,114 A | 8/1991 | Chapman et al. | |
| 5,053,036 A | 10/1991 | Perren et al. | |
| 5,127,914 A * | 7/1992 | Calderale et al. | 606/65 |
| 5,129,899 A | 7/1992 | Small et al. | |
| 5,190,544 A | 3/1993 | Chapman et al. | |
| 5,209,751 A | 5/1993 | Farris et al. | |
| 5,364,398 A | 11/1994 | Chapman et al. | |
| 5,364,399 A * | 11/1994 | Lowery et al. | 606/295 |
| 5,474,553 A | 12/1995 | Baumgart | |
| 5,484,439 A * | 1/1996 | Olson et al. | 606/65 |
| 5,578,036 A | 11/1996 | Stone et al. | |

(Continued)

FOREIGN PATENT DOCUMENTS

EP   0471419 A2   2/1992

(Continued)

*Primary Examiner* — Eduardo C Robert
*Assistant Examiner* — David Comstock
(74) *Attorney, Agent, or Firm* — Gordon & Jacobson, PC

(57) ABSTRACT

A fracture fixation plate system for use on a long bone having a metaphysis and a diaphysis, includes at least one end plate having a head portion for the metaphysis, and at least one fragment plate having a first end and a second end with a plurality of screw holes therebetween. The end plate includes mating structure adapted to mate with and securely couple to at least one end of the at least one fragment plate. The system preferably includes several end plates and fragment plates to accommodate anatomy of various sizes.

14 Claims, 8 Drawing Sheets

U.S. PATENT DOCUMENTS

| | | | |
|---|---|---|---|
| 5,601,553 A | 2/1997 | Trebing et al. | |
| 5,616,142 A | 4/1997 | Yuan et al. | |
| 5,620,445 A | 4/1997 | Brosnahan et al. | |
| 5,733,287 A | 3/1998 | Tepic et al. | |
| 5,772,662 A | 6/1998 | Chapman et al. | |
| 5,827,286 A * | 10/1998 | Incavo et al. | 606/71 |
| 5,906,644 A | 5/1999 | Powell | |
| 5,975,904 A | 11/1999 | Spiegel | |
| 6,001,099 A | 12/1999 | Huebner | |
| 6,340,362 B1 | 1/2002 | Pierer et al. | |
| 6,383,186 B1 | 5/2002 | Michelson | |
| 6,645,208 B2 | 11/2003 | Apfelbaum et al. | |
| 6,669,700 B1 | 12/2003 | Farris et al. | |
| 6,699,249 B2 | 3/2004 | Schlapfer et al. | |
| 7,604,657 B2 | 10/2009 | Orbay et al. | |
| 7,635,381 B2 | 12/2009 | Orbay | |
| 2002/0013586 A1* | 1/2002 | Justis et al. | 606/61 |
| 2003/0060828 A1 | 3/2003 | Michelson | |
| 2004/0087953 A1 | 5/2004 | Singhatat et al. | |
| 2004/0102778 A1 | 5/2004 | Huebner et al. | |
| 2004/0167521 A1* | 8/2004 | De Windt | 606/69 |
| 2004/0193155 A1 | 9/2004 | Castaneda | |
| 2004/0210221 A1* | 10/2004 | Kozak et al. | 606/69 |
| 2004/0260291 A1* | 12/2004 | Jensen | 606/69 |
| 2005/0049594 A1 | 3/2005 | Wack et al. | |
| 2005/0154392 A1 | 7/2005 | Medoff et al. | |
| 2005/0187551 A1 | 8/2005 | Orbay et al. | |
| 2005/0240187 A1 | 10/2005 | Huebner et al. | |
| 2006/0229619 A1 | 10/2006 | Orbay et al. | |
| 2006/0235404 A1 | 10/2006 | Orbay et al. | |
| 2007/0260244 A1 | 11/2007 | Wolter | |

FOREIGN PATENT DOCUMENTS

| | | |
|---|---|---|
| EP | 0773004 A1 | 5/1997 |
| FR | 2367479 A1 | 5/1978 |
| GB | 2072514 A | 10/1981 |
| JP | 11299804 | 2/1999 |
| JP | 2003052709 | 2/2003 |
| WO | WO99/44529 | 9/1999 |
| WO | WO2004/045389 A2 | 6/2004 |
| WO | WO2006/102081 A1 | 9/2006 |

* cited by examiner

MODULAR FRACTURE FIXATION PLATE SYSTEM WITH MULTIPLE METAPHYSEAL AND DIAPHYSEAL PLATES

CROSS-REFERENCE TO RELATED APPLICATIONS

This application is related to U.S. Ser. No. 10/985,598, filed Nov. 10, 2004, and U.S. Ser. No. 11/040,779, filed Jan. 21, 2005, which are hereby incorporated by reference herein in their entireties.

BACKGROUND OF THE INVENTION

1. Field of the Invention

This invention relates broadly to surgical implants. More particularly, this invention relates to a bone fracture fixation system.

2. State of the Art

Fracture to the metaphyseal portion of a long bone can be difficult to treat. Improper treatment can result in deformity and long-term discomfort.

By way of example, a Colles' fracture is a fracture resulting from compressive forces being placed on the distal radius, and which causes backward or dorsal displacement of the distal fragment and radial deviation of the hand at the wrist. Often, a Colles' fracture will result in multiple bone fragments which are movable and out of alignment relative to each other. If not properly treated, such fractures may result in permanent wrist deformity and limited articulation of the wrist. It is therefore important to align the fracture and fixate the bones relative to each other so that proper healing may occur.

Alignment and fixation of a metaphyseal fracture (occurring at the extremity of a shaft of a long bone) are typically performed by one of several methods: casting, external fixation, pinning, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Pinning with K-wires (Kirschner wires) is an invasive procedure whereby pins are positioned into the various fragments. This is a difficult and time consuming procedure that provides limited fixation if the bone is comminuted or osteoporotic. Plating utilizes a stabilizing metal plate typically placed against the dorsal side of a bone, and screws extending from the plate into holes drilled in the bone fragments to provide stabilized fixation of the fragments.

In some cases, a relatively proximal diaphyseal portion as well as the distal metaphyseal portion of the radius may be fractured. In these cases, fragment plates are often used in conjunction with the distal radius plate. There is a disadvantage, however, in using two plates rather than one. It results in unsupported bone between the two implants. The resultant load supported by the bone between the plates in a concentrated manner. Thus, it would be desirable to provide an integrated implant which shares the load across the entire implant for distal and mid-shaft fractures.

U.S. Pat. No. 5,190,544 to Chapman et al. describes a modular plating system including a metaphyseal plate and a diaphyseal plate which are interconnected via a dovetail slot and then secured to the bone with cortical bone screws to lock the plates together. The integrity of such a system is subject to loosening in the event the bone screws loosen their engagement with the bone, e.g., through micromotion. Furthermore, if the bone is of poor quality, e.g., as a result of multiple fractures along the bone portion underlying the components, integrity between the components may never be accomplished. In addition, the metaphyseal component which receives an end of the diaphyseal fragment plate is significantly thicker (approximately 75% percent thicker) and wider (approximately 35% wider) than the fragment plate, providing an undesirably thick metaphyseal plate and creating a potentially irritating transition in two dimensions from the metaphyseal plate to the diaphyseal plate where the metaphyseal plate ends.

SUMMARY OF THE INVENTION

It is therefore an object of the invention to provide a modular fixation system.

It is another object of the invention to provide a modular fixation system that desirably aligns and stabilizes multiple bone fragments in a fracture to permit proper healing.

It is also an object of the invention to provide a modular fixation system which does not rely on the bone for locking the modular components together.

It is a further object of the invention to provide a modular fixation system which will not irritate the tissue.

It is an additional object of the invention to provide an improved fixation system which accommodates the anatomical structure of the metaphysis and diaphysis of the radius.

In accord with these and other objects, which will be discussed in detail below, a fracture fixation plate system for the radius according to the invention includes a plurality of different sized distal radius plates (e.g., volar plates or dorsal plates) and a plurality of different sized fragment plates. The distal radius plates are generally T-shaped having a head and a stem substantially transverse thereto. The end of the stem is provided with a mating structure whereby an end of a fragment plate can be coupled to the distal radius plate. The surgeon can select an appropriate size distal radius plate and an appropriate size fragment plate and secure them together prior to implant to form a unified distal radius and fragment plate customized for the patient. This overcomes the disadvantage of using separate distal radius and fragment plates and allows for a wide variety of different sizes while using the minimum number of components. It is an important aspect of the invention that the distal radius plate and fragment plate be joined without reliance on the bone to join them. Otherwise, the tight interface and coupling between the plates could be compromised based on the quality of the bone, which may be fractured beneath the location of the coupling or which may be osteoporotic. In order to secure the distal radius plate and fragment plate together independent of the bone, set screw holes are provided at both ends of the fragment plates. In addition, suitable mating structure is provided at the end of the radius plate stem, e.g., a slot with an unthreaded orthogonal set screw hole. The two plates are mated by inserting an end of the fragment plate into the slot at the end of the distal radius plate stem, then inserting a set screw through the orthogonal set screw hole to engage the threaded set screw hole in the end of the fragment plate.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
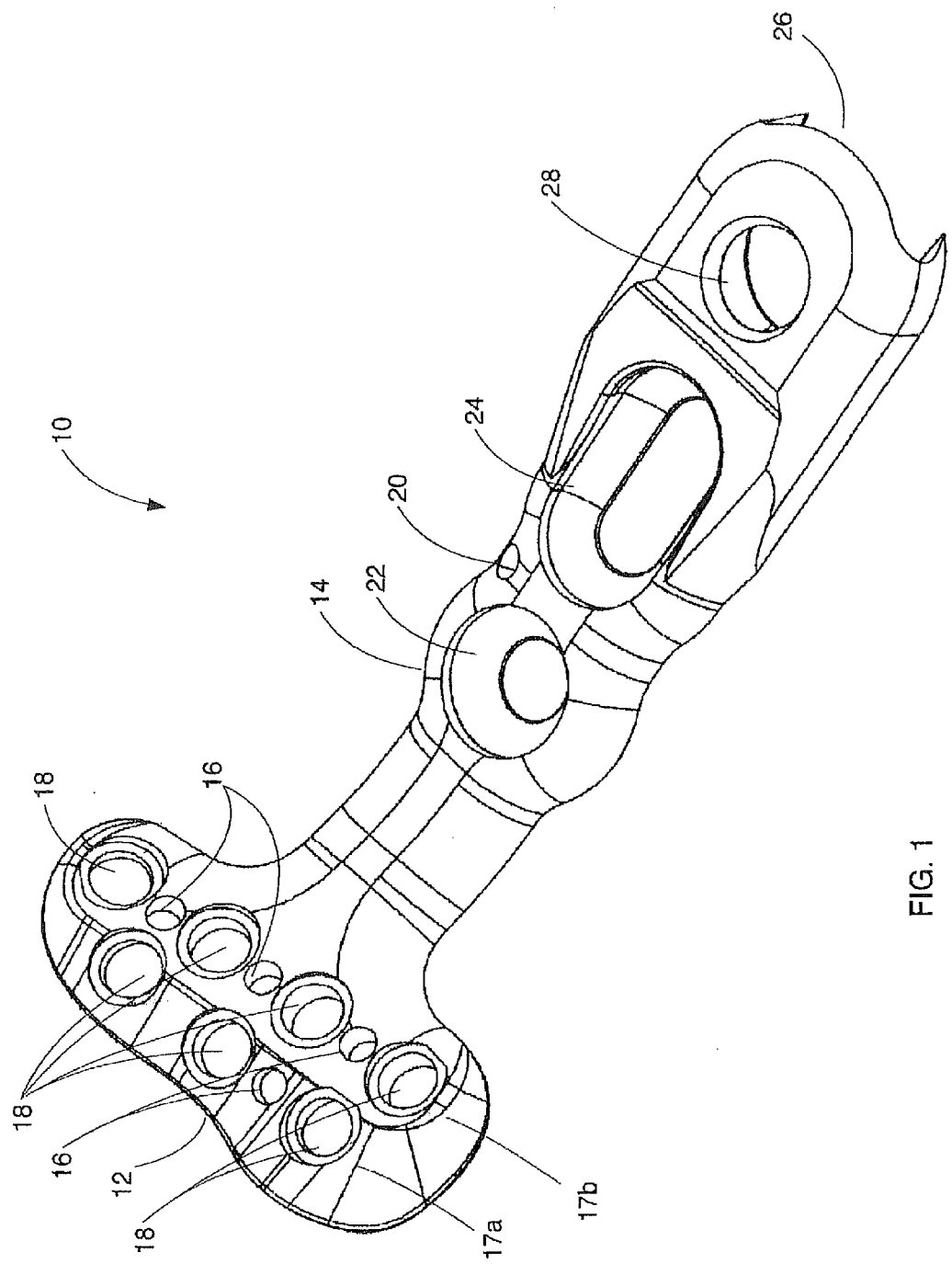
FIG. 1 is a top perspective view of a distal radius volar plate according to the invention.
Figure 2:
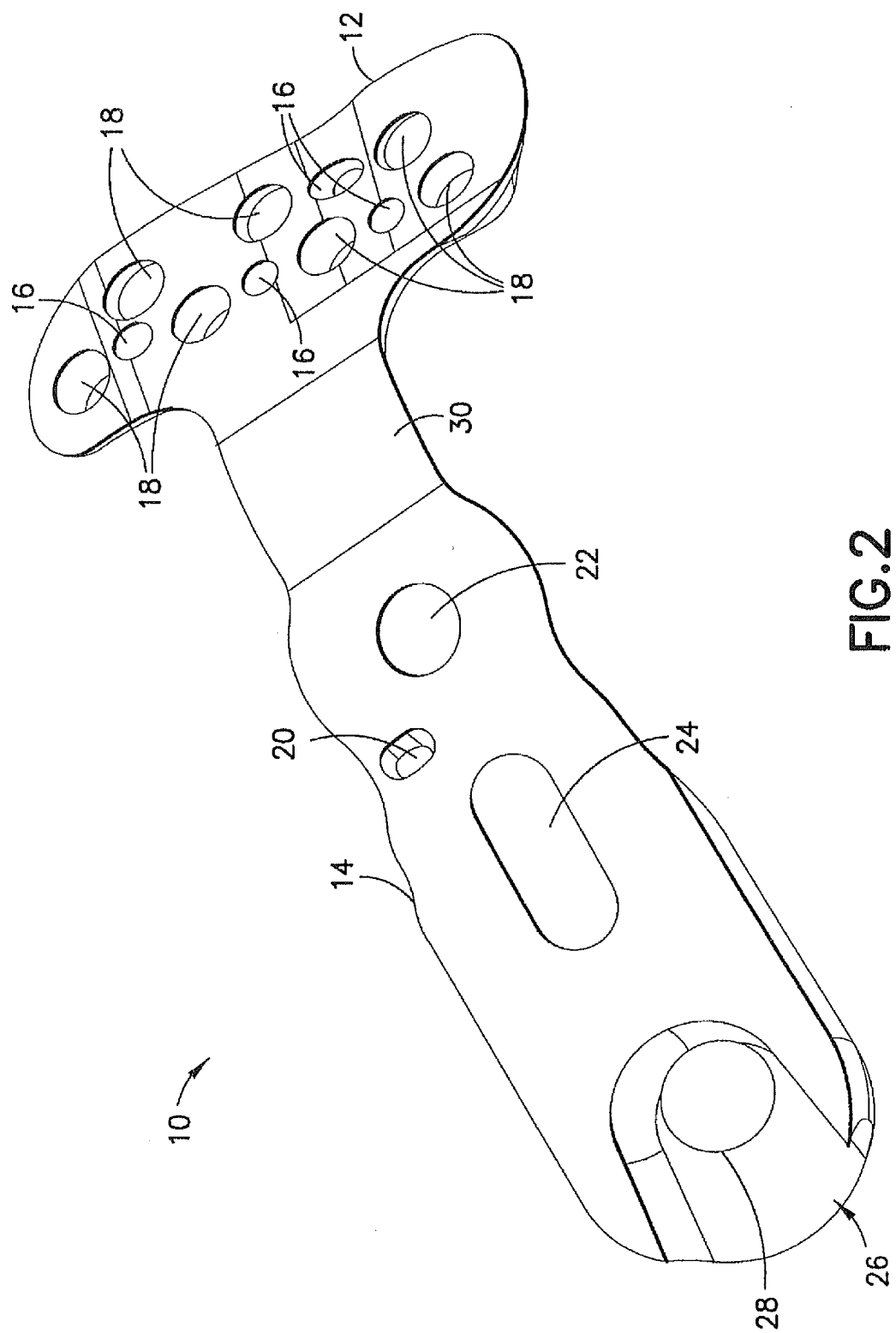
FIG. 2 is a bottom perspective view of the volar plate.

Turning now to FIGS. 1 and 2, a distal radius volar fixation plate (or generally an 'end' plate or metaphyseal plate) 10 includes a distal head portion 12 and a proximal stem portion 14. In a preferred embodiment, the plate 10 corresponds to the plate described in previously incorporated U.S. Ser. No. 10/985,598. However, other metaphyseal plates for different bones or different locations on the radius bone can be used.

The head portion 12 of the volar fixation plate 10 shown has a plurality of alignment holes 16 which are dimensioned to closely accept K-wires in a fixed angle relationship and two longitudinally offset rows 17a, 17b of screw holes 18 for receiving fixation elements therethrough. In a preferred embodiment, the screw holes 18 are threaded, and as such are specifically adapted to receive locking screws and pegs which lock relative to the plate.

The stem portion 14 has at least one alignment hole 20 dimensioned to closely accept a K-wire and may optionally include one or more (two as illustrated) bone screw holes 22, 24. That is, the stem may be substantially shorter than shown and does not need to include a bone screw hole. The free end of the stem portion 14 includes a slot 26 and an orthogonal set screw hole 28 intersecting the slot. As shown in the Figures, the slot 26 is open to the proximal end of the stem portion, and preferably is also open on the bottom side of the stem portion as well.

From the Figures, it will be appreciated that the top side (FIG. 1) of the volar plate 10 has a topography of curved surfaces and recesses surrounding some of the holes to provide a low profile when seated on the anatomical bone surface. The bottom side (FIG. 2) of the head portion 12 is likewise constructed to conform with the anatomy, while the stem portion 14 presents a smooth surface. A portion of the bottom of the head portion 12 lies in a first plane and the stem portion 14 lies in a second plane. A neck 30 transitions between the two planes. The angle between the two planes is preferably approximately 25 degrees.

The alignment holes and the bone screw holes are used as described in previously incorporated U.S. Ser. No. 10/985, 598. The slot 26 and the set screw hole 28 are used in conjunction with a fragment plate and a set screw as described in more detail below.

Figure 3:
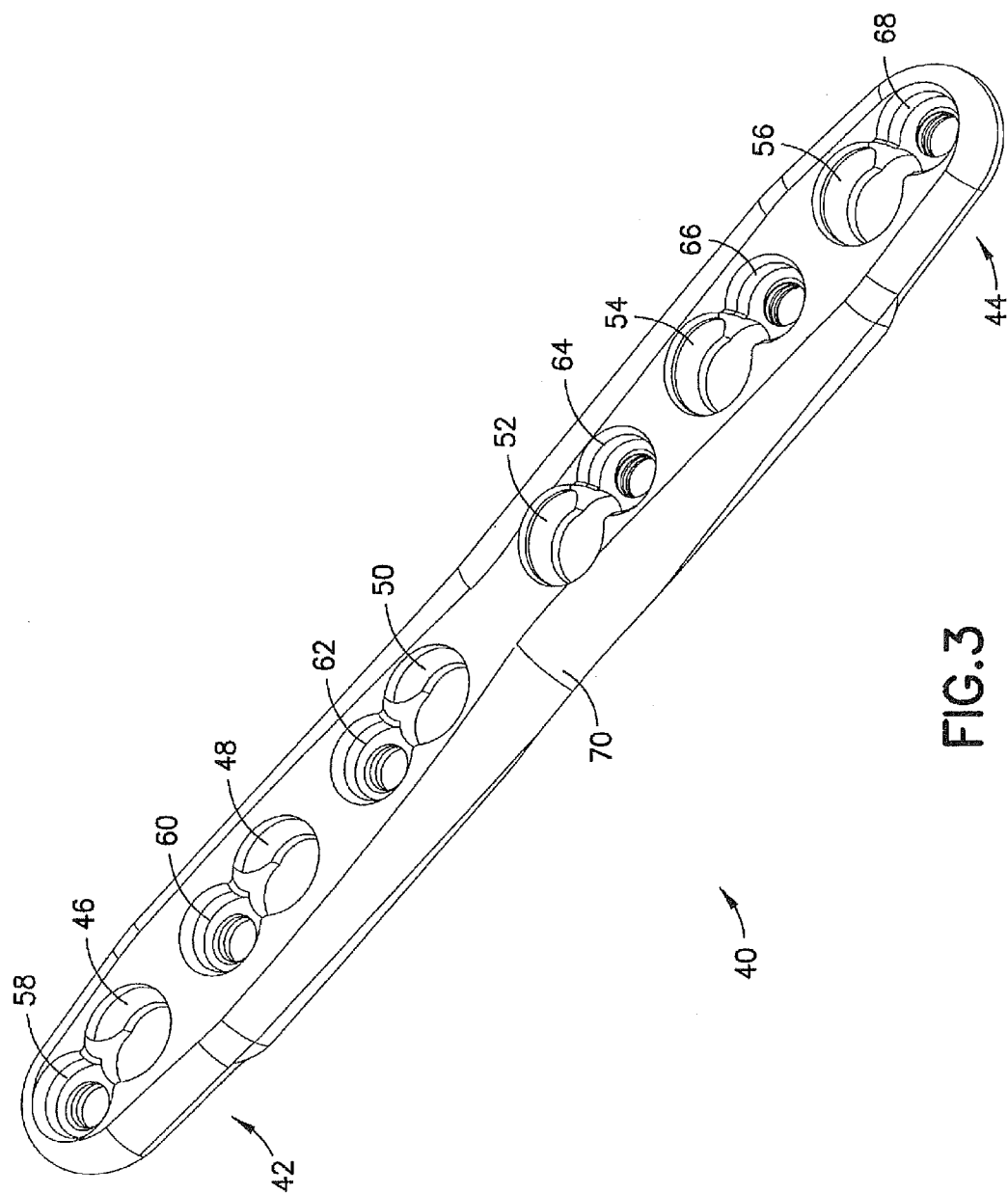
FIG. 3 is top perspective view of a fragment plate according to the invention.
Figure 4:
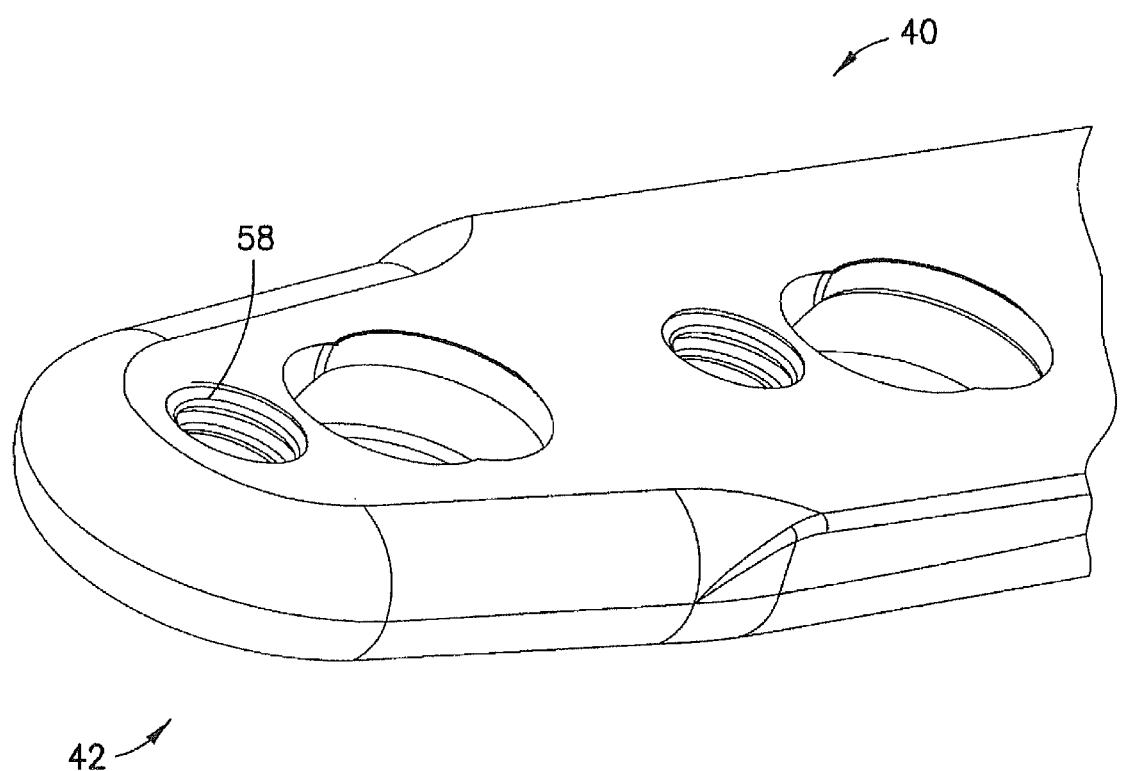
FIG. 4 is an enlarged broken bottom perspective view of an end of the fragment plate.
Figure 5:
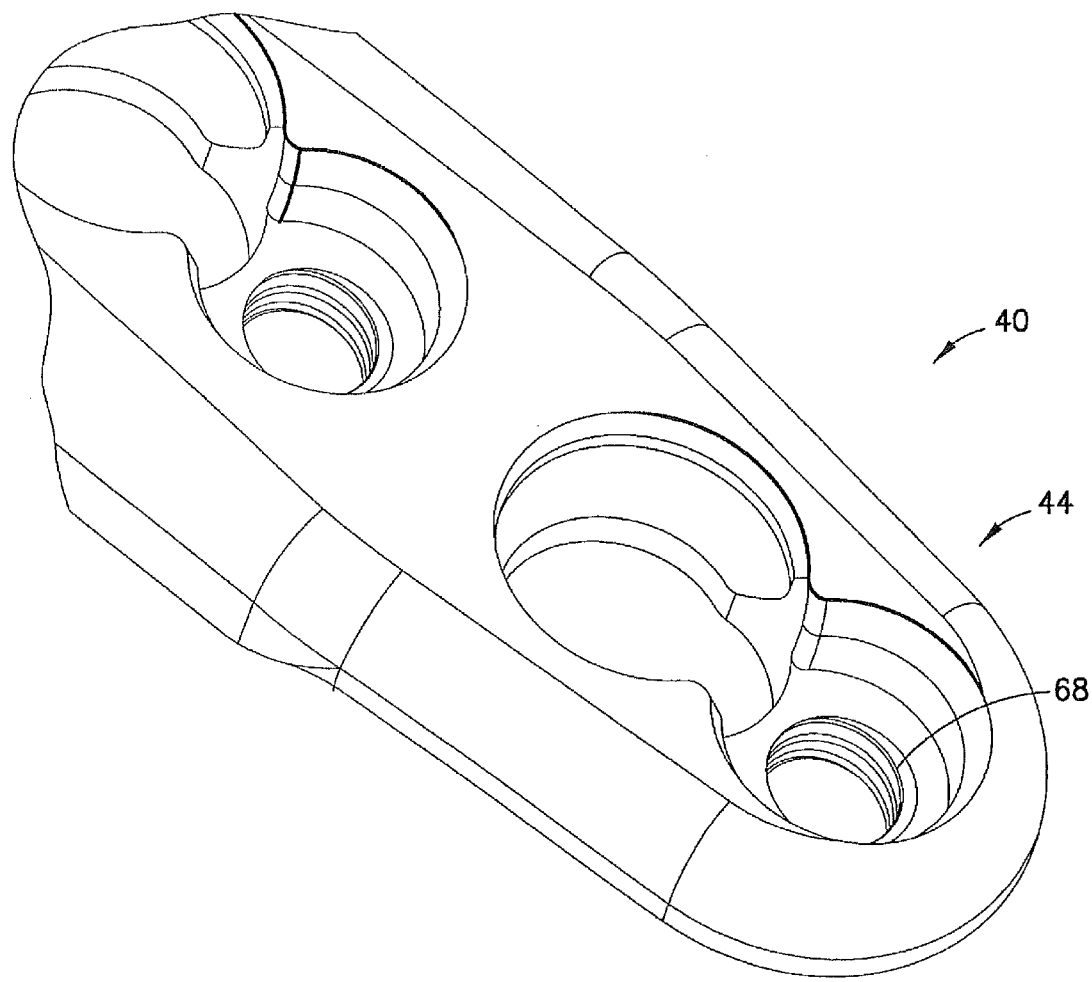
FIG. 5 is an enlarged broken top perspective view of an end of the fragment plate.

Turning now to FIGS. 3-5, an exemplary fragment plate (or diaphyseal plate) 40 according to the invention is illustrated. The fragment plate 40 is an elongate plate having a first end 42 and a second end 44. A plurality of bone screw holes 46, 48, 50, 52, 54, 56 are spaced along the length of the plate for receiving bone screws, and a threaded set screw hole 58, 60, 62, 64, 66, 68 is arranged adjacent each bone screw hole. More particularly, such screw holes are preferably any of the screw holes and associated locking systems described in previously incorporated U.S. Ser. No. 11/040,779, filed Jan. 21, 2005, for the reasons and advantages provided therein, although any suitable bone screw hole may be used.

As illustrated, the shape of the fragment plate 40 and the arrangement of holes are preferably longitudinally symmetrical about a mid point 70. Each set screw hole is provided on a side of a bone screw hole closer to an end of the fragment plate than the midpoint of the plate, with a set screw hole 58, 68 specifically being located at each end of the plate. As seen best in FIGS. 4 and 5, the ends 42, 44 of the plate are tapered as well as rounded. The taper occurs over a significant length which permits both a bone screw hole 46, 56 and a set screw hole 58, 68 to be located in the tapered ends 42, 44 of each plate. Comparing FIGS. 4 and 5 with FIGS. 1 and 2, it will be appreciated that the ends 42, 44 of the plate 40 are shaped and dimensioned to fit neatly into the slot 26 of the volar plate 10 with the set screw hole 58, 68 of the plate 40 aligning with the set screw hole 28 of the plate 10. This is illustrated more clearly in FIG. 6. The taper at the end of the fragment plate 40 permits the remainder of the fragment plate and the stem 14 of the end plate 10 to have substantially the same width, e.g., approximately 0.43" for a distal radius fixation system. It is noted that both ends 42, 44 of the fragment plate preferably have the same shape and features. Thus either end 42, 44 may be inserted into the slot 26 of the plate.

Figure 6:
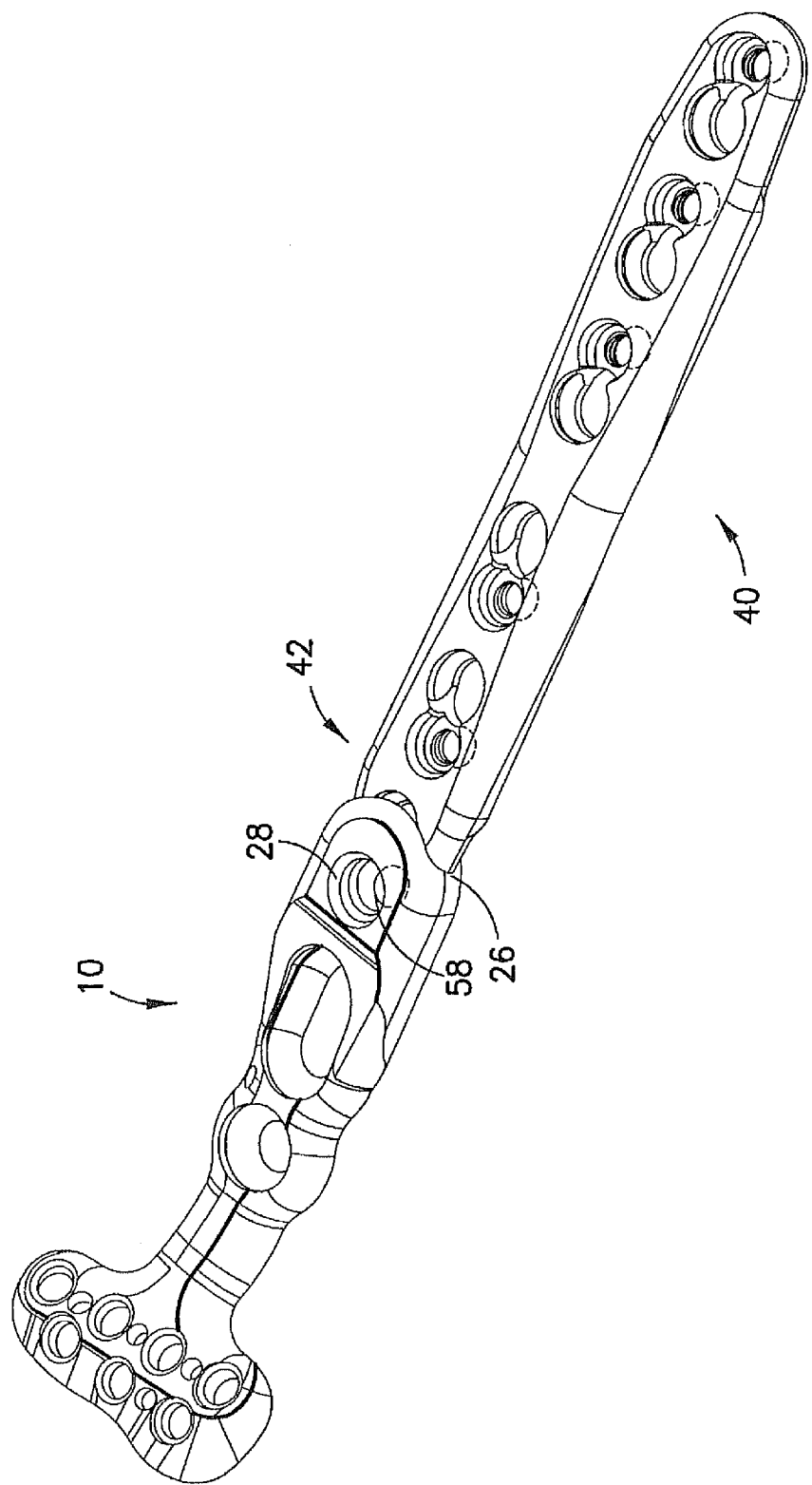
FIG. 6 is a top perspective view of the volar plate with the fragment plate inserted into the slot at the end of the volar plate stem.
Figure 7:
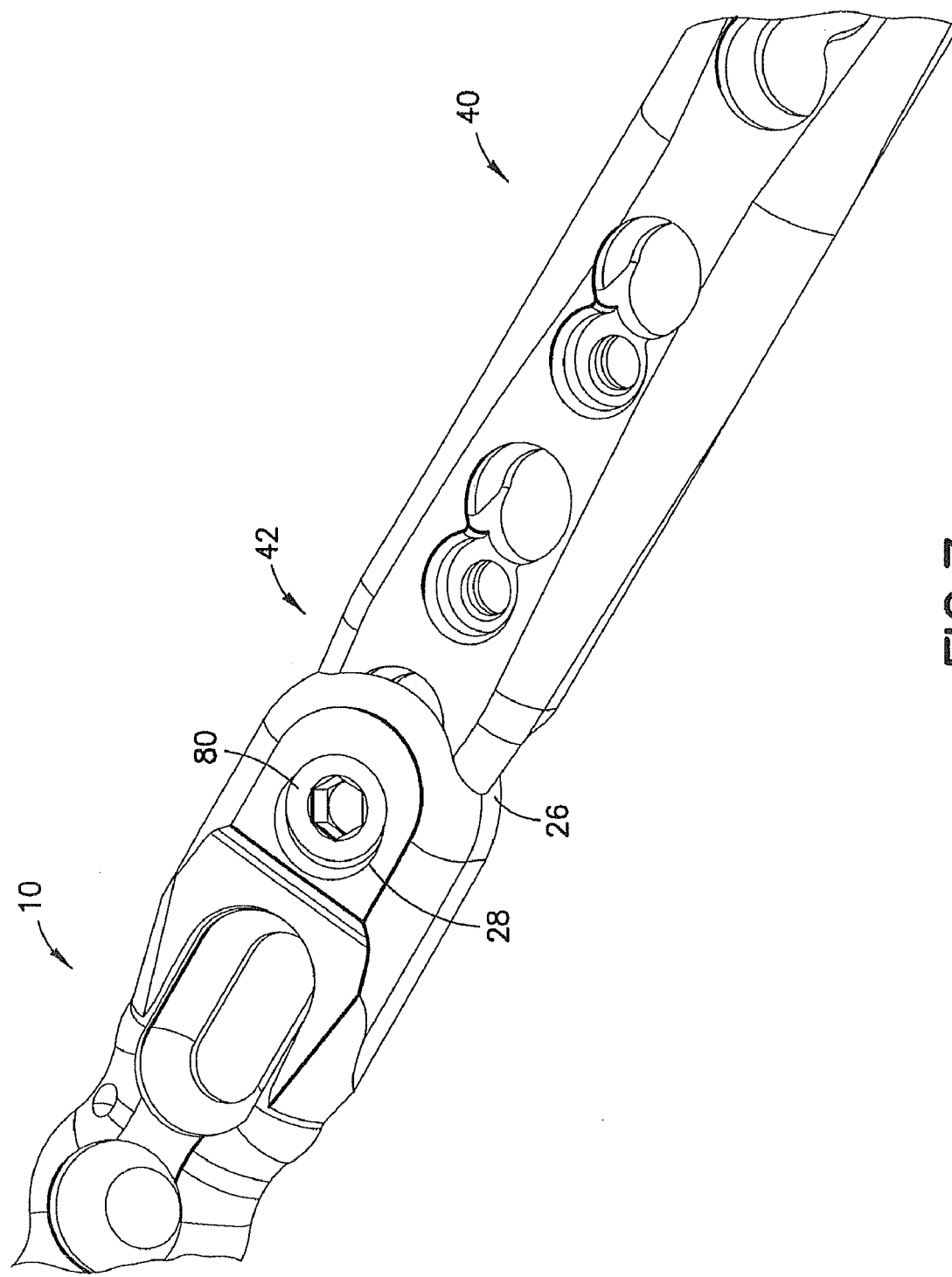
FIG. 7 is an enlarged broken top perspective view showing the mating of the volar plate and the fragment plate with a set screw.
Figure 8:
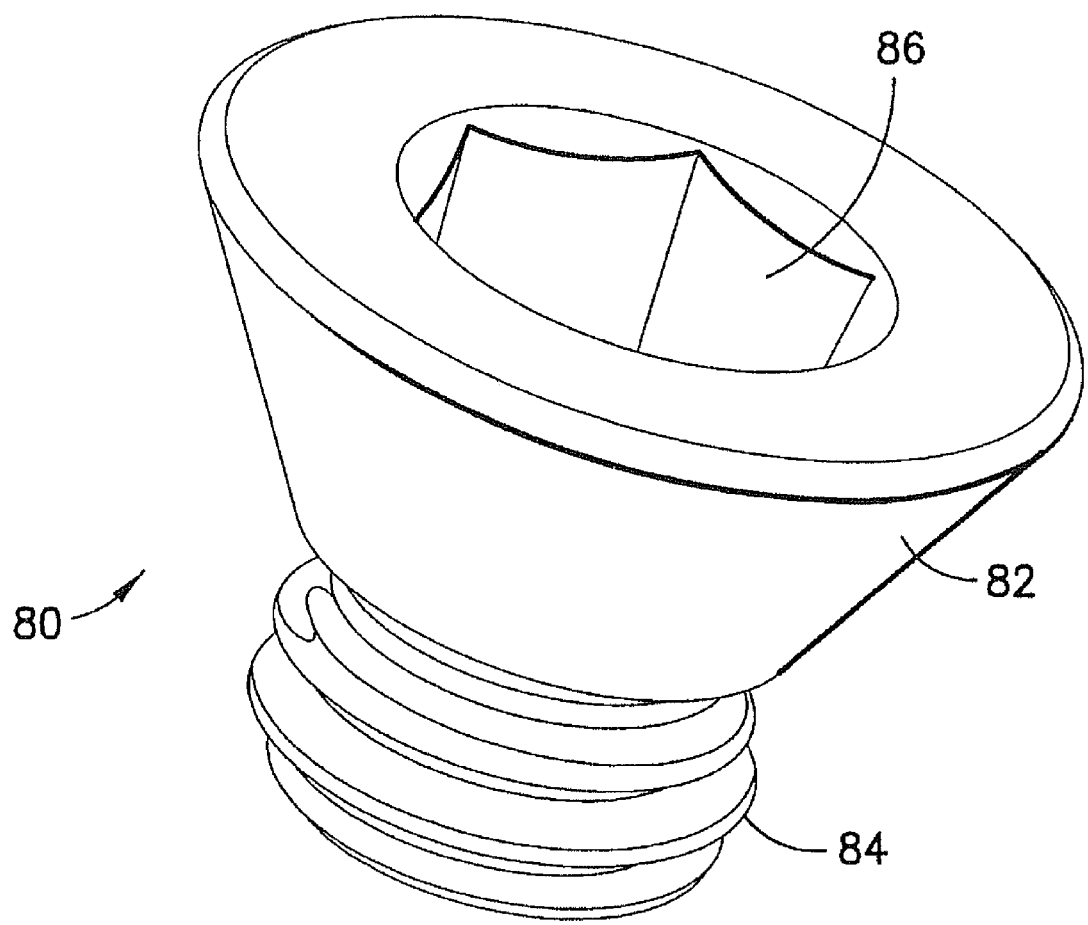
FIG. 8 is an enlarged perspective view of the set screw.

FIG. 6 shows the end 42 of the plate 40 inserted into the slot 26 of the plate 10. The tapered and rounded end 42 of the plate 40 is shaped and dimensioned to fit neatly into the slot 26 of the volar plate 10 with the threaded set screw hole 58 of the plate 40 aligning with the unthreaded set screw hole 28 of the plate 10. When the two plates are arranged as shown in FIG. 6, a set screw 80 is inserted into the hole 28 as shown in FIG. 7. When so inserted, the set screw 80 is threaded into the threaded set screw hole 58 in the plate 40. This secures the two plates together so that they function as a single piece. It is an important aspect of the invention that the distal radius plate and fragment plate be joined without reliance on the bone to join them. Otherwise, the tight interface and coupling between the plates could be compromised based on the quality of the bone, e.g., where such bone is fractured beneath the location of the coupling or where the bone is osteoporotic.

The presently preferred set screw 80 has a frustoconical head 82 from which depends a threaded stem 84. The head 82 has a hex socket 86 adapted to receive a driver (not shown). The set screw provides a secure lock between the two plates independent of the bone.

By having a threaded set screw hole 58, 68 located near each end of the fragment plate, each such hole can be used to lock the fragment plate to the volar plate, or may alternatively be used to lock an adjacent bone screw in a bone screw hole 46, 56 in place.

In accord with the invention, the end plate 10 at the slot 26 and the fragment plate 40 are substantially similar in thickness, preferably within approximately 30% of each other, and more preferably approximately 26% (end plate=0.145" and fragment plate=0.115"). The relatively close thicknesses are possible, for one reason, in that the end plate does not need to support the compressive forces of bone screws at that location. Rather, as discussed above, the set screws are used which exert a substantially smaller force on the upper thinner portion of the end plate.

According to an important aspect of the invention, the plates 10 and 40 are arranged in a kit containing several different size plates 10 and several different size fragment plates 40. According to the presently preferred embodiment, three different size volar plates are provided: standard, wide, and narrow. A plurality of different length fragment plates are also provided. The fragment plates may be straight or curved. For example, the plate may be curved in the plane of the plate to match the radius of curvature of the volar side of the radius bone, e.g., r=23 inches over approximately eighty percent of the length of the plate. The fragment plates can be used alone or in combination with the volar plates. When used together, distal and mid-shaft fractures can be covered with one integral plate (i.e. the two plates coupled to each other as shown in FIG. 7). Thus, the loads are shared by the combined plate rather than the bone between two plates. The load is thereby spread out rather than concentrated on the bone between two plates. The modularity of the different size plates allows for the assembly of a wide variety of combinations using only a few different sizes. For example, three different width volar plates packed together with five different length fragment plates can be used to construct fifteen different size combination plates using only eight different size pieces.

According to an alternate embodiment of the invention, the volar plate is not required to include a socket for receiving an end portion of the fragment plate. Rather, a discrete coupler with sockets at two of its sides can be provided between the volar and fragment plates. The coupler operates to "splice" together the metaphyseal volar plate and the diaphyseal fragment plate. The advantage is that the volar plate for use in the system can be a standard component without modification, and can therefore be used alone without the fragment plate. Thus, the surgical tray will need fewer of the more expensive volar plates. In addition, the coupler allows "splicing" of multiple diaphyseal fragment plates together to make one extra long plate.

There have been described and illustrated herein embodiments of a fixation plate, and particularly plates for fixation of distal radius fractures. While particular embodiments of the invention have been described, it is not intended that the invention be limited thereto, as it is intended that the invention be as broad in scope as the art will allow and that the specification be read likewise. Thus, while particular preferred materials, dimensions, and relative angles for particular elements of the system have been disclosed, it will be appreciated that other materials, dimensions, and relative angles may be used as well. Further, while the invention has been described with respect to distal volar radius plates, the invention may include other 'end' plates suitable in size and shape for placement at other metaphyseal locations, e.g., the dorsal side of the distal radius, the humerus, the femur and the tibia. In addition, end plates having shapes other than a 'T' may also be used, such as lateral and medial columns (generally 'L'-shaped), and plates having a flared or forked head, provided such end plates are dimensioned and configured for placement at the metaphysis. In addition, while a particular number of screw holes in the end plate and fragment plate have been described, it will be understood a different numbers of screw holes may be used. Also, fewer or more threaded holes (for pegs or locking screws) may be used. In addition, while a particular preferred angle between the head and stem of the volar plate has been disclosed, other angles can also be used. It will therefore be appreciated by those skilled in the art that yet other modifications could be made to the provided invention without deviating from its spirit and scope.

What is claimed is:

1. A fracture fixation plate system for use on a long bone having a metaphysis and a diaphysis, comprising:
   a) at least one end plate having a head portion for the metaphysis defining a plurality of fixation holes for receiving fixation elements that extend into the bone a slot and an unthreaded set screw hole intersecting said slot;
   b) at least one fragment plate having a first end and a second end with a plurality of bone screw holes therebetween, and a threaded set screw hole, said fragment plate having an end dimensioned to fit into said slot such that said threaded screw hole is aligned with said unthreaded hole; and
   c) a set screw having a head and a threaded shaft, said head seating in said unthreaded set screw hole and said shaft threaded into said threaded set screw hole so that said set screw securely longitudinally retains said end plate and fragment plates together in tension, independently of the bone.

2. The system according to claim 1, wherein:
said at least one end plate is a plurality of plates having head portions of different sizes,
said at least one fragment plate is a plurality of different length fragment plates,
said end plates and said fragment plates adapted to be mixed and matched and coupled to each other.

3. The system according to claim 1, wherein:
said fixation holes are threaded to receive fixation elements which lock relative to said head portions of said at least one end plate.

4. The system according to claim 1, wherein:
said end plate includes a stem angled relative to said head portion, and said mating structure is integrated into said stem.

5. The system according to claim 1, wherein:
said unthreaded hole is orthogonal relative to said slot.

6. The system according to claim 1, wherein:
said end plate includes a plurality of alignment holes adapted to closely receive K-wires in a substantially fixed angle relationship.

7. The system according to claim 1, wherein:
said fragment plate has a longitudinal axis and is longitudinally symmetrical about the midpoint of the longitudinal axis.

8. The system according to claim 1, wherein:
said bone screw holes of said fragment plate are non-threaded bone screw holes, and
said fragment plate has a plurality of second threaded set screw holes corresponding in number to said plurality of said bone screw holes, each second set screw hole being adjacent a respective bone screw hole.

9. The system according to claim 8, wherein:
said fragment plate includes a longitudinal midpoint, and for each bone screw hole, each said second set screw hole is provided on a side of the bone screw hole closer to an end of the fragment plate than the midpoint.

10. The system according to claim 1, wherein:
said at least one end of said fragment plate is tapered to fit said mating structure.

11. The system according to claim 1, wherein:
the head portion is sized and shaped for the distal volar radius bone.

12. The system according to claim 1, wherein:
said fragment plate is curved along its longitudinal axis.

13. The system according to claim 1, wherein:
said fragment plate is curved along its longitudinal axis to match the radius of curvature of the volar side of the radius bone.

14. The system according to claim 1, wherein:
said end plate and said fragment plate are securely longitudinally retainable relative to each other independently of any compression fastener which couples at least one of said end plate and said fragment plate to the bone.

* * * * *